US00PP09215P

United States Patent [19]

Klemm

[11] Patent Number: Plant 9,215

[45] Date of Patent: Jul. 25, 1995

[54] GERANIUM PLANT KLESPRI

[76] Inventor: Siegfried Klemm, Hanfäcker 8, D 70378 Stuttgart, Germany

[21] Appl. No.: 285,866

[22] Filed: Aug. 4, 1994

[51] Int. Cl.[6] ..... A01H 5/00

[52] U.S. Cl. ..... Plt./87.12

[58] Field of Search ..... Plt. 87.12

[56] References Cited

U.S. PATENT DOCUMENTS

P.P. 6,064 12/1987 Winner ..... Plt./87.12

P.P. 8,669 3/1994 Trees ..... Plt./87.12

P.P. 8,760 5/1994 Schumann ..... Plt./87.12

*Primary Examiner*—James R. Feyrer

*Attorney, Agent, or Firm*—Arnold, White & Durkee

[57] ABSTRACT

Geranium Klespri is a new and distinct cultivar of geranium, botanically known as *Pelargonium* × *zonale* Hybriden. It is distinguished from other geranium plants by its bright red color, zonated leaves and vigorous and upright habit.

1 Drawing Sheet

BACKGROUND OF THE NEW PLANT

Klespri is a product of a controlled breeding program that had the objective of developing new geranium red flowering cultivars with double or semidouble flowers, good precocity, floral richness, bright flower color, good zonation, compact growth habit and high market value.

Klespri originated from an unknown pollen parent and the seed parent PAC Bruni. PAC Bruni was bred from PAC Dresden in the 1980's and to the inventor's knowledge is not protected under Breeder's Rights.

The new cultivar was discovered in 1987 and selected by the inventor as one flowering plant from among the progeny of the seed parent Bruni grown in a controlled environment in Stuttgart, Germany. The seed from Bruni was obtained after cultivation of Bruni with a group of red flowering cultivars that were pollinated with each other. Klespri differed from its seed parent in having a lighter red flower color and showing more vigor than the parent.

Compared with its seed parent Bruni, the new cultivar Klespri grows with the same density as the parent but is taller and larger in size. Bruni has semidouble red flowers that show dark red spots on the petals while Klespri's flower color is also red but lighter in color with a very elegant appearance. Both Klespri and Bruni flower eary and uniformly.

The first act of asexual reproduction of Klespri was accomplished when vegetative cuttings were taken from the initial selection in controlled environment in Stuttgart, Germany by technicians working under the supervision of the inventor. Horticultural examination of selected plants demonstrated that the combination of characteristics herein disclosed from Klespri are firmly fixed and are retained through successive generations of asexual reproduction.

Klespri has not been observed under all possible environmental conditions. The phenotype may vary significantly with variations in environment such as temperature, light intensity and day length. The following observations, measurements and comparisons describe plants grown in Stuttgart, Germany under conditions that approximate those used in commercial practice. Similar characteristics are found when the plant is grown under controlled environmental conditions in Italy and the Netherlands.

Of the many varieties of the same species of geranium plant, the new cultivar Klespri showed better floral richness than the red varieties trialed at the time of the first trial of Klespri in 1988. Of these same species, Klespri most closely resembles PAC Isabell.

Klespri shows regular compact growth with perennial quality. This characteristic is popular with home gardeners and is a sales advantage to nurserymen who deal directly with consumers. Additionally, Klespri plants show good transportability because the flowers are resistant to shattering. The flowrs do not fade out in heat or rot under damp conditions, thus showing good weather resistance. The leaves are somewhat resistant to Botrytis, thus requiring less care and expense in cultivation.

Klespri flowers continuously from spring to fall, whether or not old clusters are removed. From the trials and marketing experience so far, the new cultivar does well in all climates that are suitable for growing geraniums. Propagation characteristics are very good as indicated by cutting production and rooting time. Rooted cuttingse transport very well.

Flower color of the new cultivar is red, clear, bright and in good contrast to the foliage. Umbels become well filled in appearance due to the wide petals of the flowers in the cluster. The number of single flowers in a cluster is not extremely large and is normal for this species. The doubleness of a single flower consists of several wide petals so that the shape of the single flower is cup-like and has an orderly appearance. The appearance of the foliage, uniformity of leaf size, leaf form and zonation are attractive and commercially desirable characteristics. Overall, the plant has a harmonious appearance which depends on the relation between plant size, leaves, umbels, stem length, etc. Market value in countries other than the United States has continued to increase since its introduction in 1988.

DESCRIPTION OF THE PHOTOGRAPH

The accompanying color photograph of Klespri illustrates typical inflorescence and leaf characteristics of the new plant. The plant was photographed using professional photographic techniques. The view is taken against a light background that illustrates flower color closest to the color values in accordance with The Royal Horticultural Society Colour Chart. The light background highlights the leaf characteristics.

DESCRIPTION OF THE PLANT

The following description uses colour reference from The Royal Horticultural Society Colour Chart. The color values were determined under prevailing conditions of natural daylight in a greenhouse environment during the month of March in Stuttgart, Germany.

The following traits have been repeatedly observed and are determined to be basic characteristics of Klespri that in combination distinguish this geranium as a new and distinct cultivar. These characteristics include a semidouble bright red flower colour that contrasts against the distinctly zoned foliage, a long indoor stem length of 140–170 mm, very good branching, and a vigorous and upright habit.

Classification:
- *Botanical.*—*Pelargonium* × *zonale* Hybriden.
- *Commercial.*—Klespri, Zonal Geranium.

The Plant

Form: Bush.
Shape: Round, symmetrical.
Height: 240–260 mm at maturity (typically September in Germany), vigorous upright habit.
Growth: Vigorous, upright, average growth rate by comparison with similar commercial varieties.
Time from rooted cutting to flowering: 91 days.
Precocity: Early.
Pinching to induce branching: Not required.
Stem length: 140–170 mm (indoors); 120–120 mm (outdoors).
Internode length: 10–15 mm.
Leaf stem length: 40–60 mm.
Branching character: Very good.
Number of stems perstalk: 2 (when marketable).
Number of stalks per plant: 7 (when marketable).
Foliage:
- *Quantity.*—Abundant, robust, zonated leaves.
- *Shape.*—Round.
- *Margin type.*—Bicrenated.
- *Size.*—80×80 mm.
- *Texture.*—Old leaves.— Leathery. Young leaves-.—Smooth. Zonation.—Glossy.
- *Color.*—Upper side.—146A. Under side.—146B. Zonation.—200C. Becomes very dark when the plants are grown where nights are cold.
- Leaf pedicles (stems).—40–60 mm.

Inflorescence

Blooming habit: Continuous (spring to fall) and profuse (new flowers appear without pinching. Unpinched umbels will dry and fall off).
Cluster size (measured when more than 20 florets are open):
- *Diameter.*—90–100 mm.
- *Depth.*—60–70 mm.

Cluster shape: Round.
Petalage: Average 10.
Florets:
- *Number of florets/cluster.*—50–60.
- *Size.*—Average length 2.3 cm; width 2.2–2.4 cm; diameter averages 4.5 cm.
- *Fullness.*—Semidouble.
- *Shape.*—Cup-shaped when first open becoming flat with maturity.
- *Perfect.*—Both pistils and stamens present.
- *Petal arrangement.*—Imbricated.
- *Petal form.*—Broad.
- *Margin type.*—Entire.
- *Petal persistence.*—5–6 days if floret not pollinated.
- *Texture.*—Soft.
- *Appearance.*—Satiny.
- *Color.—outer petal: Body.*—40A. Base.—40A. Reverse side.—40C. Inside petal: Body.—40A. Base.—40A. Reverse side.—40A.

Petaloids:
- *Number.*—1–2.
- *Color.*—40A.
- *Size.*—Length is 0.3–0.5 cm; width is 0.5–0.9 cm.

Flower stem:
- *Pedicel posture.*—Ascending with the opening of the flower.
- *Pedicel thickness.*—About like those of the species and sufficiently strong to position the flowers as they open.
- *Pedicel arrangement.*—Radiate from the apex of the peduncle as typical of most members of the species.
- *Length.*—2.5 cm.
- *Pedicel color.*—Green.
- *Sepal color.*—Green with brown-red basal part when florets open.
- *Discoloration after full bloom.*—Not noticeable.
- *Effect of heat or rain.*—Negligible. Flowers and leaves are resistant to hot weather. The flower color does not fade out under hot and sunny weather conditions. Leaves maintain their color even in hot weather. Flowers and leaves are also resistant to rain. The flowers maintain their color during periods of rainy weather. The flowers mature normally and do not turn brown. Botrytis is rare.

Sepals:
- *Shape.*—Long and pointed.
- *Number.*—5.

Color:
- *Inside.*—143C.
- *Outside.*—146C.

Number of buds and flowering clusters:
- *Young plants.*—2 buds, 3 clusters (April when plants start to flower and are marketable). Plants are judged marketable when the plant shows about three clusters with some open florets and also about two clusters that show only buds.
- *Number of clusters observed between April and the middle of May.*—Average about 12 clusters.
- *Number of clusters from middle of May to end of September.*—70–75 clusters on each plant. More plants are produced in hot summers.

Persistence: Some petals fall down when the flowers dry. Later the whole cluster falls depending on weather conditions. Florets fall only under vey windy conditions.
Disease resistance: Shows some resistance to Botrytis.
Fragrance: None.
Bud:
- *Average diameter.*—10 mm.
- *Average depth.*—15 mm.
- *Shape.*—Ovoid.
- *Color (inside).*—143C.
- *Color (outside).*—146C.

Reproductive organs:

*Stamens.*—6–7 arranged around the ovaries.

*Anthers.*—2.5 mm.

*Filaments.*—7–8 mm.

*Pistils.*—1 with 5–6 branches.

*Styles: Length.*—9 mm. Color.—Dark pink (upper), ovaries. — Green.

*Stigmas.*—Light red.

*Fertile.*—Yes.

*Length of seed.*—3–4.5 mm.

*Color of seed.*—Brown.

Spring flowering response period: 91 days from rooted cutting to flowering stage under commercial greenhouse conditions.

Outdoor flower production: Continuously from spring to fall: 70–100 per cluster (middle of May to end of September).

Durability: High degree of weather tolerance.

What is claimed is:

1. A new and distinct geranium cultivar, substantially as herein described and shown, characterized by its bright red flower colour and good zonation.

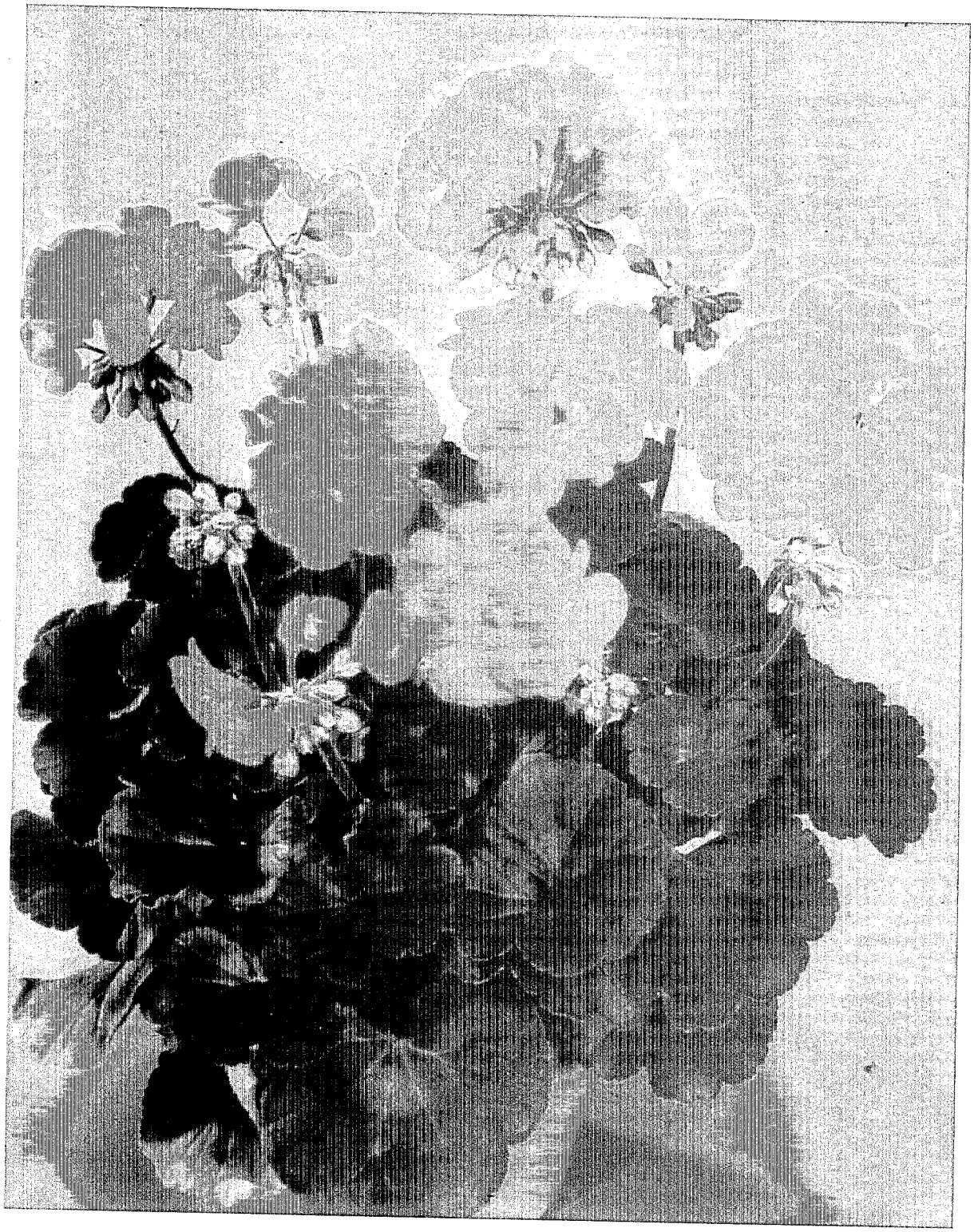

* * * * *